United States Patent
Tsuruta et al.

(10) Patent No.: US 8,827,896 B2
(45) Date of Patent: Sep. 9, 2014

(54) ENDOSCOPE APPARATUS AND MEDICAL SYSTEM

(71) Applicant: Olympus Medical Systems Corp., Tokyo (JP)

(72) Inventors: Misa Tsuruta, Hachioji (JP); Satoshi Takekoshi, Hachioji (JP); Takeo Suzuki, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/928,961

(22) Filed: Jun. 27, 2013

(65) Prior Publication Data
US 2013/0345513 A1 Dec. 26, 2013

Related U.S. Application Data

(63) Continuation of application No. PCT/JP2012/072768, filed on Sep. 6, 2012.

(30) Foreign Application Priority Data

Feb. 17, 2012 (JP) .................................. 2012-032903

(51) Int. Cl.
| | |
|---|---|
| *A61B 1/04* | (2006.01) |
| *A61B 1/06* | (2006.01) |
| *A61B 1/00* | (2006.01) |
| *A61B 5/00* | (2006.01) |
| *A61B 17/28* | (2006.01) |
| *A61B 5/107* | (2006.01) |
| *A61B 17/29* | (2006.01) |
| *A61B 19/00* | (2006.01) |

(52) U.S. Cl.
CPC ........... *A61B 1/0638* (2013.01); *A61B 1/00009* (2013.01); *A61B 1/00045* (2013.01); *A61B 1/043* (2013.01); *A61B 5/0071* (2013.01); *A61B 5/0084* (2013.01); *A61B 17/28* (2013.01); *A61B 5/1076* (2013.01); *A61B 5/4238* (2013.01); *A61B 5/4887* (2013.01); *A61B 17/29* (2013.01); *A61B 2019/5441* (2013.01)
USPC ........................... 600/118; 600/109; 600/178

(58) Field of Classification Search
CPC .. A61B 1/00009; A61B 1/043; A61B 1/0638; A61B 5/1076; A61B 5/0071
USPC .................. 600/109, 117, 118, 178, 476–478
See application file for complete search history.

(56) References Cited

U.S. PATENT DOCUMENTS

| | | | | |
|---|---|---|---|---|
| 4,980,763 A | * | 12/1990 | Lia | .................................. 348/67 |
| 5,047,848 A | * | 9/1991 | Krauter | ........................... 348/82 |

(Continued)

FOREIGN PATENT DOCUMENTS

| | | |
|---|---|---|
| JP | 07-281105 A | 10/1995 |
| JP | 2003-111722 A | 4/2003 |

(Continued)

*Primary Examiner* — John P. Leubecker
(74) *Attorney, Agent, or Firm* — Scully, Scott, Murphy & Presser, P.C.

(57) ABSTRACT

An endoscope apparatus includes: a light source apparatus that emits light in a wavelength band including a first wavelength band for exciting a first fluorescent substance and a second wavelength band; an image pickup section that picks up an image of first fluorescence emitted when the first fluorescent substance is excited and an image of second fluorescence emitted when a second fluorescent substance provided on a treatment instrument is excited, to generate a fluorescence image; an information storing section that stores shape information including information on a shape of the second fluorescent substance; and an operation section that performs an operation to estimate an actual size of a region in which the first fluorescence is generated, based on a scaling factor calculated based on the shape information and a size of a draw region of the second fluorescence, and a size of a draw region of the first fluorescence.

20 Claims, 9 Drawing Sheets

(56) References Cited

U.S. PATENT DOCUMENTS

| | | | |
|---|---|---|---|
| 5,202,758 A * | 4/1993 | Tamburrino | 348/68 |
| 5,573,492 A * | 11/1996 | Dianna et al. | 600/117 |
| 5,669,871 A | 9/1997 | Sakiyama | |
| 5,967,968 A * | 10/1999 | Nishioka | 600/117 |
| 8,553,076 B2 * | 10/2013 | Chan | 348/68 |
| 2002/0026093 A1* | 2/2002 | Ooyatsu | 600/118 |
| 2005/0240077 A1* | 10/2005 | Rovegno | 600/108 |
| 2007/0161854 A1* | 7/2007 | Alamaro et al. | 600/109 |
| 2009/0097725 A1* | 4/2009 | Krupnik et al. | 382/128 |
| 2010/0092054 A1* | 4/2010 | Hensley et al. | 382/128 |
| 2012/0289778 A1* | 11/2012 | Chan | 600/109 |
| 2014/0046129 A1* | 2/2014 | Boutillette et al. | 600/104 |

FOREIGN PATENT DOCUMENTS

| | | |
|---|---|---|
| JP | 2008-245838 A | 10/2008 |
| JP | 2010-259582 A | 11/2010 |
| JP | 2011-110272 A | 6/2011 |
| JP | 2011-136005 A | 7/2011 |

\* cited by examiner

| PHOSPHOR | | TYPE AND ACTUAL SIZE OF FORCEPS |
|---|---|---|
| SHAPE | FLUORESCENCE WAVELENGTH BAND | |
| EQUILATERAL TRIANGLE ACTUAL LENGTH OF ONE SIDE emm | E1nm~ E2nm | TYPE A $\phi$=Pmm |
| EQUILATERAL TRIANGLE ACTUAL LENGTH OF ONE SIDE emm | E3nm~ E4nm | TYPE A $\phi$=Qmm |
| STRIP SHAPE ACTUAL LENGTH OF WIDTH fmm | E1nm~ E2nm | TYPE B $\phi$=Pmm |
| ⋮ | ⋮ | ⋮ |

ENDOSCOPE APPARATUS AND MEDICAL SYSTEM

CROSS REFERENCE TO RELATED APPLICATION

This application is a continuation application of PCT/JP2012/072768 filed on Sep. 6, 2012 and claims benefit of Japanese Application No. 2012-032903 filed in Japan on Feb. 17, 2012, the entire contents of which are incorporated herein by this reference.

BACKGROUND OF THE INVENTION

1. Field of the Invention

The present invention relates to an endoscope apparatus and a medical system, and specifically relates to an endoscope apparatus and a medical system that enable observation of fluorescence generated from a fluorescent substance inside a living body.

2. Description of the Related Art

Diagnosis methods using a fluorescent medical agent targeting biological protein specifically expressed in a predetermined lesion such as cancer have conventionally been known. More specifically, for example, a diagnosis method in which excitation light is applied to a subject part inside a living body with a fluorescent medical agent administered thereto in advance, fluorescence emitted from the subject part upon the application of the excitation light is received, and a diagnosis of, e.g., whether or not a lesion exists in the subject part is made with reference to a fluorescence image generated based on the received fluorescence has conventionally been known.

On the other hand, for example, Japanese Patent Application Laid-Open Publication No. 2011-136005 discloses a technique in which an image of a mark provided on a treatment instrument placed in the vicinity of a subject part is picked up and distance information between the subject part and a distal end of an insertion portion of an endoscope is obtained based on the size of the picked-up mark image in a medical system.

SUMMARY OF THE INVENTION

An endoscope apparatus according to an aspect of the present invention includes: a light source apparatus that emits excitation light in a wavelength band including a first wavelength band for exciting a first fluorescent substance accumulated in a subject part inside a body cavity and a second wavelength band that is different from the first wavelength band; an image pickup section configured so as to pick up an image of first fluorescence emitted when the first fluorescent substance accumulated in the subject part is excited by light in the first wavelength band and an image of second fluorescence emitted when a second fluorescent substance provided on a treatment instrument via which treatment of the subject part is performed is excited by light in the second wavelength band, to generate a fluorescence image; an information storing section that stores shape information including information on a shape of the second fluorescent substance; and an operation section that performs an operation to calculate a scaling factor based on the shape information and a size of a draw region of the second fluorescence in the fluorescence image, and further performs an operation to estimate an actual size of a region in which the first fluorescence is generated, based on the calculated scaling factor and a size of a draw region of the first fluorescence in the fluorescence image.

A medical system according to an aspect of the present invention includes: a light source apparatus that emits excitation light in a wavelength band including a first wavelength band for exciting a first fluorescent substance accumulated in a subject part inside a body cavity and a second wavelength band that is different from the first wavelength band; a treatment instrument including a second fluorescent substance that is excited by light in the second wavelength band, the treatment instrument being configured so as to enable treatment of the subject part to be performed; an image pickup section configured so as to pick up an image of first fluorescence emitted, upon application of the excitation light, from the first fluorescent substance accumulated in the subject part, and an image of second fluorescence emitted, upon the application of the excitation light, from the second fluorescent substance arranged in a vicinity of the subject part, to generate a fluorescence image; an information storing section that stores shape information including information on a shape of the second fluorescent substance; and an operation section that performs an operation to calculate a scaling factor based on the shape information and a size of a draw region of the second fluorescence in the fluorescence image, and further performs an operation to estimate an actual size of a region in which the first fluorescence is generated, based on the calculated scaling factor and a size of a draw region of the first fluorescence in the fluorescence image.

DETAILED DESCRIPTION OF THE PREFERRED EMBODIMENT

An embodiment of the present invention will be described below with reference to the drawings.

Figure 1:
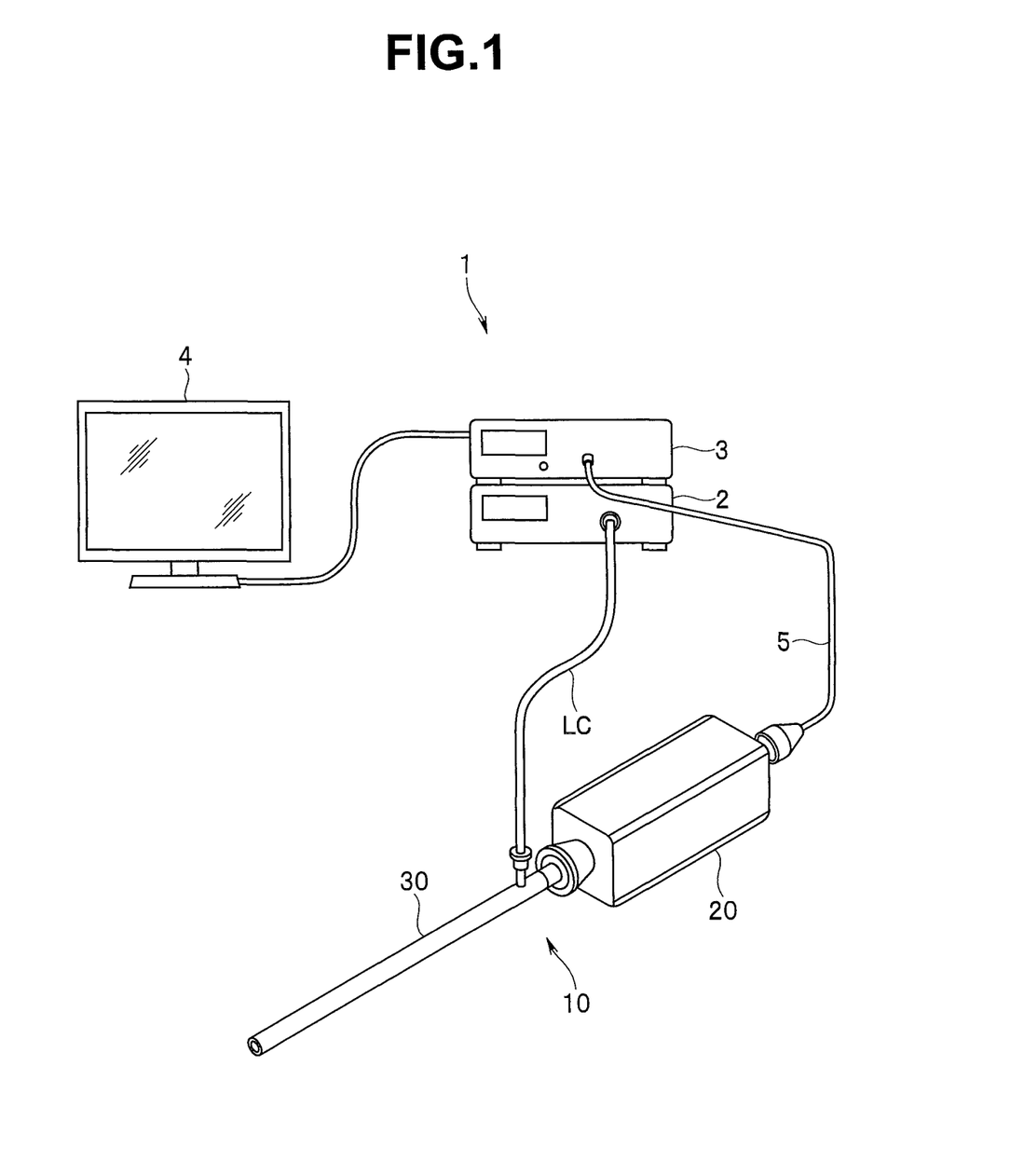
FIG. 1 is a diagram illustrating an example of a configuration of a main part of an endoscope apparatus according to an embodiment of the present invention.

FIGS. 1 to 14 relate to an embodiment of the present invention. FIG. 1 is a diagram illustrating an example of a configuration of a main part of an endoscope apparatus according to an embodiment of the present invention.

As illustrated in FIG. 1, an endoscope apparatus 1 includes: a light source apparatus 2 capable of supplying excitation light for fluorescence observation and white light for white light observation as illuminating light; a rigid endoscope image pickup apparatus 10 that applies the illuminating light supplied from the light source apparatus 2 to an object, picks up an image of return light emitted from the object upon the application of the illuminating light and outputs the image according to the picked-up return light; an image processing apparatus 3 that performs various processing on the image outputted from the rigid endoscope image pickup apparatus 10; and a monitor 4 that displays, e.g., an image processed by the image processing apparatus 3.

As illustrated in FIG. 1, the rigid endoscope image pickup apparatus 10 includes a rigid insertion portion 30 to be inserted into a body cavity, and an image pickup unit 20 that picks up an image of return light from an object to which light is guided by the rigid insertion portion 30. Also, as illustrated in FIG. 1, the rigid endoscope image pickup apparatus 10 is configured so that: the light source apparatus 2 and the rigid insertion portion 30 can be connected via an optical cable LC; and the image processing apparatus 3 and the image pickup unit 20 can be connected via a cable 5.

The rigid insertion portion 30 has an elongated cylindrical shape that can be inserted into a body cavity of an examinee. Also, at a rear end portion of the rigid insertion portion 30, respective connection members (not illustrated) that allow the image pickup unit 20 and the optical cable LC to be detachably connected thereto are provided.

On the other hand, although not illustrated, in the rigid insertion portion 30, a light guide configured to convey illuminating light supplied from the light source apparatus 2 via the optical cable LC to a distal end portion of the rigid insertion portion 30, an illumination window configured to apply the illuminating light conveyed via the light guide to an object from the distal end portion of the rigid insertion portion 30, and a lens group configured to guide return light emitted from the object upon the application of the illuminating light to the rear end portion of the rigid insertion portion 30 are provided, respectively.

Figure 2:
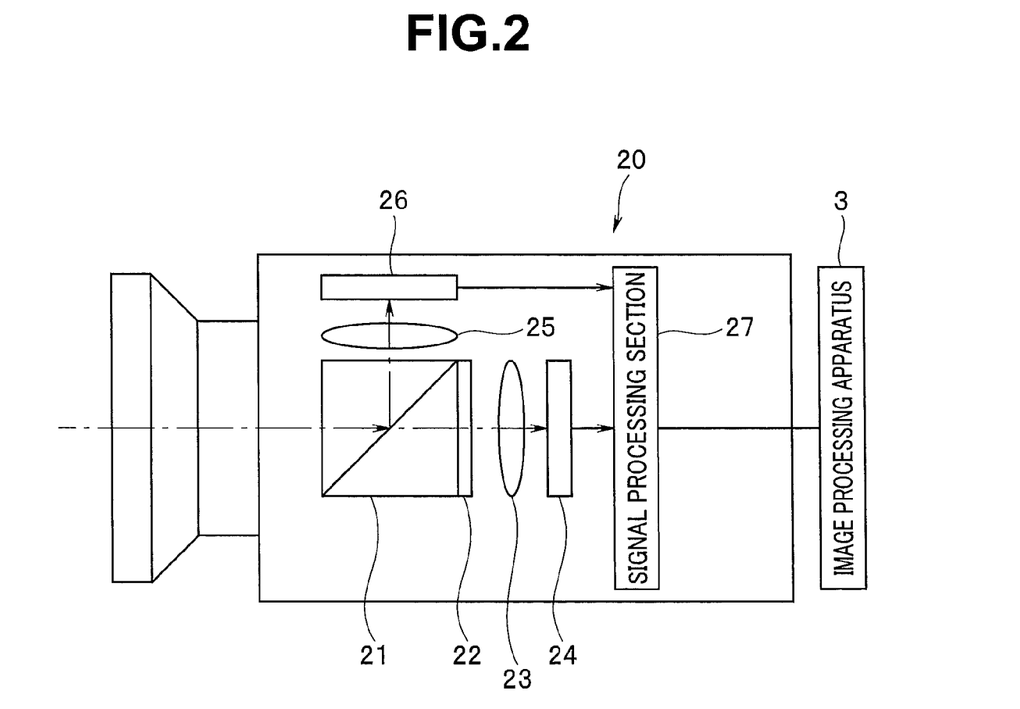
FIG. 2 is a diagram illustrating an example of a configuration of an image pickup unit according to the present embodiment.

FIG. 2 is a diagram illustrating an example of a configuration of an image pickup unit according to the present embodiment.

As illustrated in FIG. 2, the image pickup unit 20 includes a fluorescence image pickup system that picks up an image of fluorescence that is return light guided via the lens group inside the rigid insertion portion 30 at the time of fluorescence observation to generate a fluorescence image, and a white light image pickup system that picks up an image of reflected light of white light that is return light guided via the lens group inside the rigid insertion portion 30 at the time of white light observation to generate a white right image. Optical axes of the fluorescence image pickup system and the white light image pickup system are separated into two optical axes by a dichroic prism 21 having spectrum characteristics of reflecting white light and transmitting fluorescence, so as to be perpendicular to each other.

The fluorescence image pickup system in the image pickup unit 20 includes an excitation light cut filter 22 having a spectrum characteristic of cutting light in a wavelength band that is the same as a wavelength band (later-described wavelength bands EW1 and EW2) of excitation light emitted from the light source apparatus 2, an image forming optical system 23 that forms an image of fluorescence transmitted by the dichroic prism 21 and the excitation light cut filter 22, and an image pickup device 24 that picks up the image of fluorescence formed by the image forming optical system 23.

The image pickup device 24, which is a monochrome highly-sensitive image pickup device, picks up an image of fluorescence formed by the image forming optical system 23 to generate a fluorescence image according to the picked-up fluorescence and outputs the fluorescence image.

Also, the white light image pickup system in the image pickup unit 20 includes an image forming optical system 25 that forms an image of white light reflected by the dichroic prism 21, and an image pickup device 26 that picks up the image of the white light formed by the image forming optical system 25.

The image pickup device 26 includes an RGB color filter provided on an image pickup surface thereof, picks up an image of white light formed by the image forming optical system 25, generates a white light image according to the picked-up white light and outputs the white light image.

On the other hand, the image pickup unit 20 includes a signal processing section 27 that performs predetermined signal processing (correlated double sampling processing, gain adjustment processing and A/D conversion processing) on the fluorescence image outputted from the image pickup device 24 and the white light image outputted from the image pickup device 26, and further outputs the fluorescence image and the white light image subjected to the predetermined signal processing, to the image processing apparatus 3 (via the cable 5).

Figure 3:
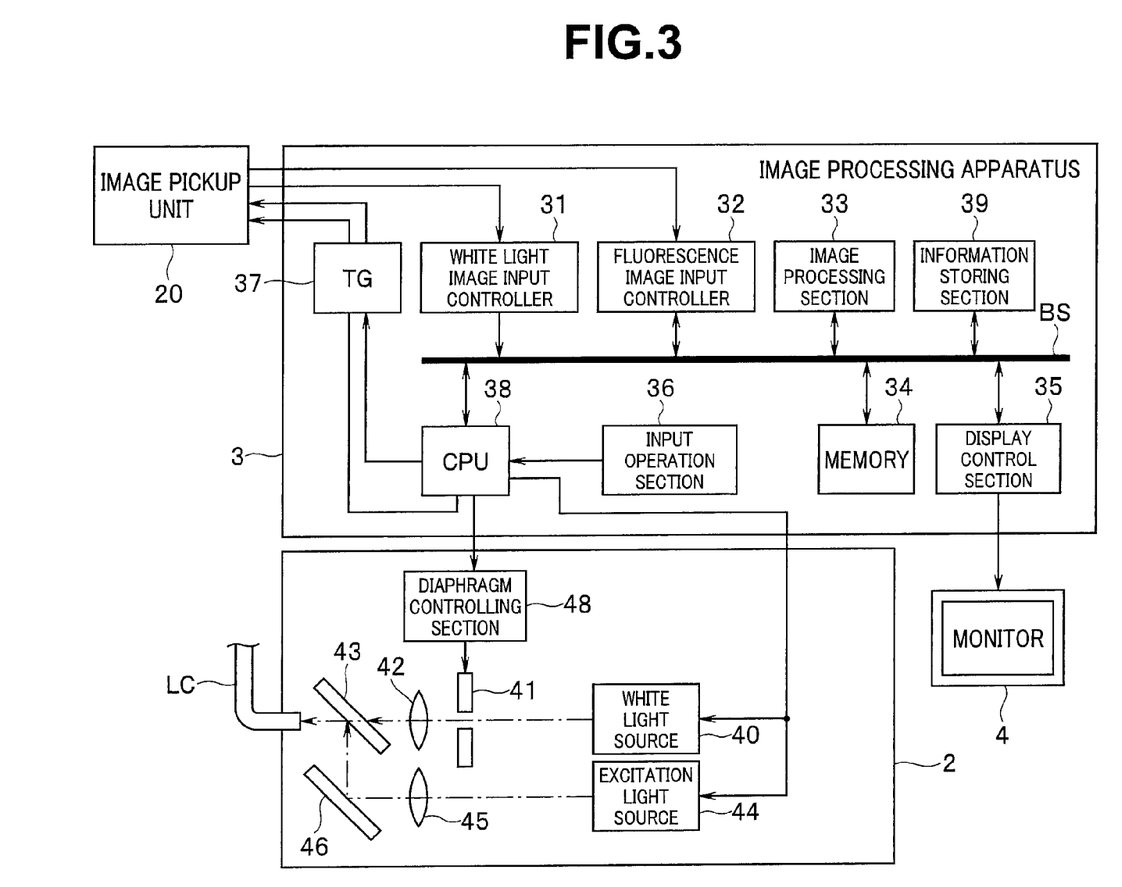
FIG. 3 is a diagram illustrating an example of configurations of an image processing apparatus and a light source apparatus according to the present embodiment.

FIG. 3 is a diagram illustrating an example of configurations of an image processing apparatus and a light source apparatus according to the present embodiment.

As illustrated in FIG. 3, the image processing apparatus 3 includes a white light image input controller 31, a fluorescence image input controller 32, an image processing section 33, a memory 34, a display control section 35, an input operation section 36, a TG (timing generator) 37, a CPU 38 and an information storing section 39.

The white light image input controller 31, which includes a line buffer having a predetermined capacity, is configured to be able to temporarily store a white light image for each frame, which is outputted from the signal processing section 27 in the image pickup unit 20. The white light image stored in the white light image input controller 31 is stored in the memory 34 via a bus BS inside the image processing apparatus 3.

The fluorescence image input controller 32, which includes a line buffer having a predetermined capacity, is configured to temporarily store a fluorescence image for each frame, which is outputted from the signal processing section 27 in the image pickup unit 20. The fluorescence image stored in the fluorescence image input controller 32 is stored in the memory 34 via the bus BS.

The image processing section 33 is configured to read an image stored in the memory 34, perform predetermined image processing on the read image and output the resulting image to the bus BS.

The display control section 35 is configured to perform various processing on the image outputted from the image processing section 33, according to, e.g., control performed by the CPU 38 to generate a video signal and output the generated video signal to the monitor 4.

The input operation section 36 includes various types of input interfaces via which various types of instructions according to input operations of a surgeon or the like can be provided to the CPU 38. More specifically, the input operation section 36 includes, for example, an observation mode selection switch that enables provision of an instruction for switching between white light observation and fluorescence observation.

The TG 37 is configured to output a drive pulse signal for driving the image pickup devices 24 and 26 in the image pickup unit 20.

The CPU 38 is configured to perform various types of control and processing according to, e.g., instructions provided via the input operation section 36.

If the CPU 38 detects that an instruction for performing white light observation is provided via the observation mode selection switch in the input operation section 36, the CPU 38 controls the TG 37 so as to drive the image pickup device 26 and stop driving of the image pickup device 24 in the image pickup unit 20. Also, if the CPU 38 detects that an instruction for performing white light observation is provided via the observation mode selection switch in the input operation section 36, the CPU 38 performs control so that the white light source 40 in the light source apparatus 2 emits light and the excitation light source 44 stops light emission.

If the CPU 38 detects that an instruction for performing fluorescence observation is provided via the observation mode selection switch in the input operation section 36, the CPU 38 controls the TG 37 so as to drive the image pickup device 24 in the image pickup unit 20 and stop driving of the image pickup device 26. Also, if the CPU 38 detects that an instruction for performing fluorescence observation is provided via the observation mode selection switch in the input operation section 36, the CPU 38 performs control so as to drive the excitation light source 44 of the light source apparatus 2 and stop driving of the white light source 40.

The CPU 38 is configured to, at the time of fluorescence observation, perform processing for obtaining observation assist information for assisting the fluorescence observation, based on a fluorescence image subjected to the predetermined image processing by the image processing section 33 and information stored in the information storing section 39 and controls the display control section 35 so as to display the obtained observation assist information on the monitor 4. Note that details of the processing for obtaining such observation assist information will be described later.

In the information storing section 39, various types of information (which will be described later), which is used when the CPU 38 performs processing for obtaining observation assist information, are stored in advance.

On the other hand, as illustrated in FIG. 3, the light source apparatus 2 includes a white light source 40 that includes, e.g., a xenon lamp that emits broadband white light, a condenser lens 42 that collects the white light emitted from the white light source 40, and a dichroic mirror 43 configured to transmit the white light collected by the condenser lens 42, reflect excitation light, which will be described later, and further make the white light and the excitation light fall on an incident end of the optical cable LC. Also, between the white light source 40 and the condenser lens 42, a diaphragm 41 that operates to provide an aperture amount according to control performed by a diaphragm controlling section 48 is provided.

Also, as illustrated in FIG. 3, the light source apparatus 2 includes an excitation light source 44 configured to emit excitation light in a wavelength band including a wavelength band EW1 for exciting a fluorescent medical agent administered to an examinee and a wavelength band EW2 for exciting a phosphor 161 provided at a predetermined position of a forceps 6, which will be described later, a condenser lens 45 that collects the excitation light emitted from the excitation light source 44, and a mirror 46 that reflects the excitation light corrected by the condenser lens 45 toward the dichroic mirror 43. Note that in the present embodiment, the wavelength band EW1 and the wavelength band EW2 are different from (do not overlap) each other.

In other words, in the endoscope apparatus 1 having such a configuration as described above, when an instruction for performing white light observation is provided via the input operation section 36 (at the time of white light observation), a white light image (color image) according to a white light is displayed on the monitor 4. Also, in the endoscope apparatus 1 having such configuration as described above, when an instruction for performing fluorescence observation is provided via the input operation section 36 (at the time of fluorescence observation), a fluorescence image (monochrome image) according to a fluorescence and observation assist information obtained by processing performed by the CPU 38 are jointly displayed on the monitor 4.

Note that the endoscope apparatus 1 according to the present embodiment is not limited to one having such a configuration that enables obtainment of a white light image and a fluorescence image, and may be, for example, one having such a configuration that enables obtainment of a fluorescence image only.

Figure 4:
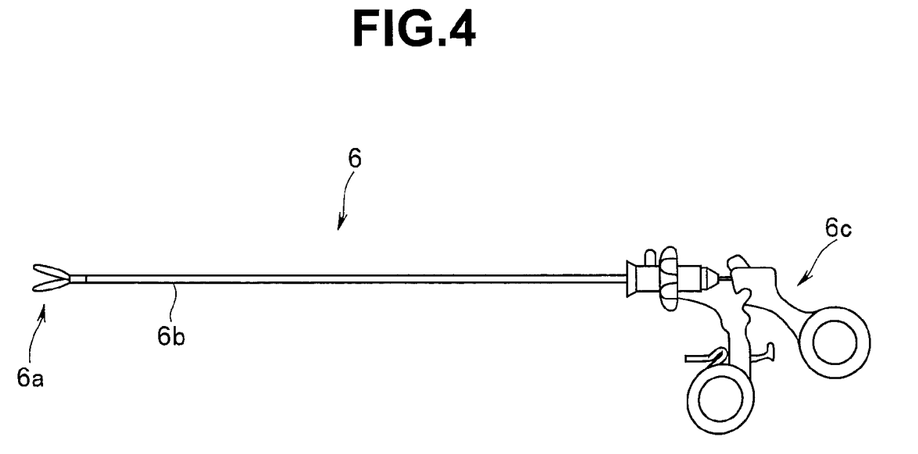
FIG. 4 is a diagram illustrating an example of a configuration of a forceps according to the present embodiment.

Incidentally, in the present embodiment, when treatment is made for a subject part inside a body cavity of an examinee, for example, the forceps 6 such as illustrated in FIG. 4 is used together with the endoscope apparatus 1. FIG. 4 is a diagram illustrating an example of a configuration of a forceps according to the present embodiment.

Figure 5:
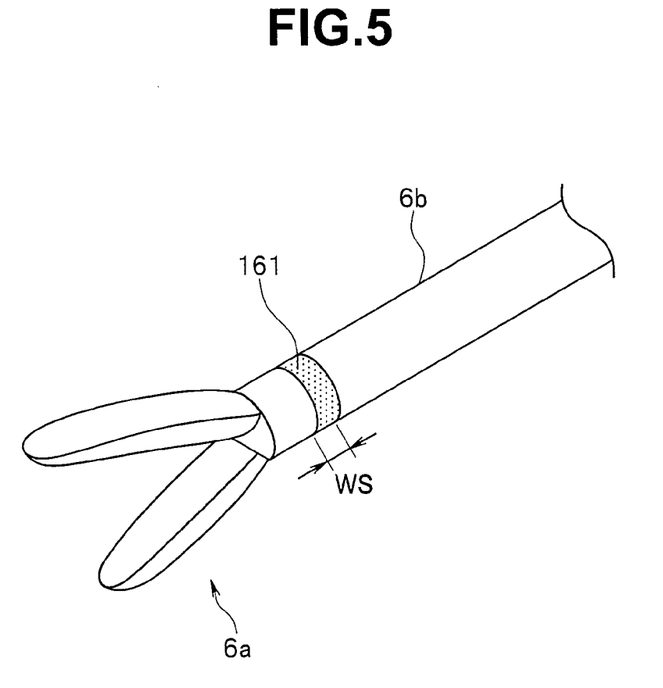
FIG. 5 is a diagram illustrating an example of a configuration of a part around a treatment portion of the forceps in FIG. 4.

As illustrated in FIG. 4, the forceps 6 includes a treatment portion 6a configured so as to enable treatment of a subject part to be performed by, e.g., grasping a tissue, and a shaft portion 6b having an elongated cylindrical shape, and an operation portion 6c via which an operation to make the treatment portion 6a work can be performed, which are successively provided in this order from the distal end side. FIG. 5 is a diagram illustrating an example of a configuration of a part around a treatment portion of the forceps in FIG. 4.

Also, on an outer circumferential face in the vicinity of the treatment portion 6a at a distal end portion of the shaft portion 6b, a phosphor 161, which is excited by light in the wavelength band EW2 included in excitation light emitted from the light source apparatus 2, is provided. More specifically, the phosphor 161 has, for example, a strip shape with a width of an actual length (actual dimension) WS such as illustrated in FIG. 5.

Note that in the present embodiment, a wavelength band (hereinafter also referred to as "wavelength band FW1") of fluorescence emitted when a fluorescent medical agent administered to an examinee in advance is excited by light in the wavelength band EW1 and a wavelength band (hereinafter also referred to as "wavelength band FW2") of fluorescence emitted when the phosphor 161 on the forceps 6 is excited by light in the wavelength band EW2 are different from (do not overlap) each other. Also, in the present embodiment, the respective wavelength bands are set to prevent fluorescence in the wavelength bands FW1 and FW2 from being cut by the excitation light cut filter 22.

Next, an operation of the present embodiment will be described. Note that hereinafter, for simplicity, a description of processing and operation during fluorescence observation will be provided specifically and a description of processing and operation at the time of white light observation will be omitted as appropriate. Also, hereinafter, for simplicity, a description will be provided below on the premise that a fluorescent medical agent that is excited by light in the wavelength band EW1 is administered to an examinee in advance and the administered fluorescent medical agent is sufficiently accumulated in (a lesion part existing in) a subject part.

Figure 6:
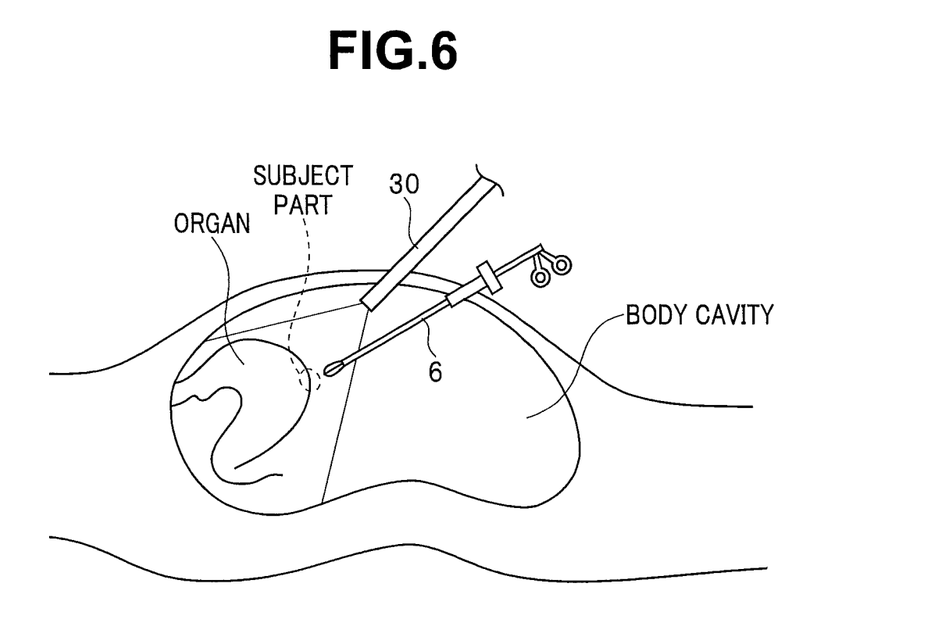
FIG. 6 is a diagram illustrating an example of a case where a rigid insertion portion and the forceps according to the present embodiment are inserted into a body cavity to perform treatment of a subject part.

First, as illustrated in FIG. 1 as an example, a surgeon or the like connects respective parts of the endoscope apparatus 1 and supplies power to the respective parts, and then provides an instruction for performing white light observation via the observation mode selection switch in the input operation section 36. FIG. 6 is a diagram illustrating an example of a case where a rigid insertion portion and a forceps are inserted into a body cavity to perform treatment of a subject part.

Figure 7:
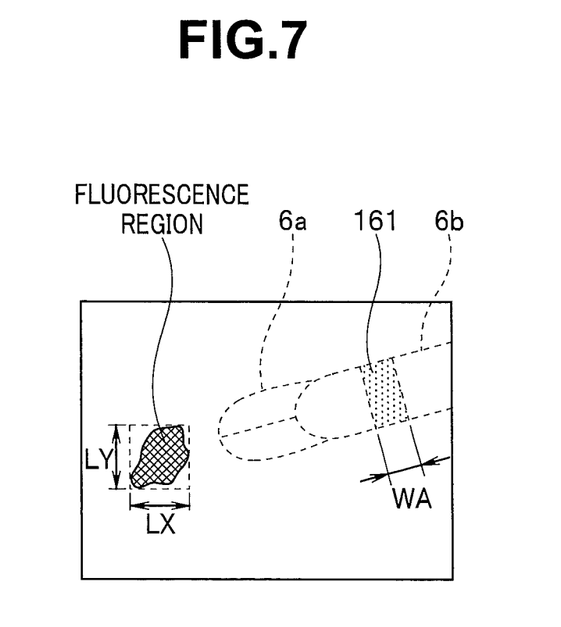
FIG. 7 is a diagram illustrating an example of a fluorescence image used in processing performed by the image processing apparatus according to the present embodiment.

Subsequently, while the surgeon or the like views a white light image displayed on the monitor 4, the surgeon or the like inserts the rigid insertion portion 30 and the forceps 6 into a body cavity of the examinee via trocars (not illustrated) installed at mutually-different positions of a body wall of the examinee, and, for example, as illustrated in FIG. 6, moves the distal end portion of the rigid insertion portion 30 and the treatment portion 6a of the forceps 6 closer to an organ in the body cavity where a subject part exists. FIG. 7 is a diagram illustrating an example of a fluorescence image used for processing in the image processing apparatus according to the present embodiment.

Furthermore, the surgeon or the like moves the distal end portion of the rigid insertion portion 30 to a position where a white light image including the subject part and the phosphor 161 of the forceps 6, for example, such as illustrated in FIG. 7, can be displayed on the monitor 4 and then provides an instruction for performing fluorescence observation via the observation mode selection switch in the input operation section 36.

Then, in response to such an instruction for performing fluorescence observation, excitation light (illuminating light) including the wavelength bands EW1 and EW2 is applied from the distal end portion of the rigid insertion portion 30 to the subject part, and upon the application of the excitation light, fluorescence in the wavelength band FW1 is emitted from a region of the subject part in which the fluorescent medical agent is accumulated (hereinafter also simply referred to as "fluorescence region"), and fluorescence in the wavelength band FW2 is emitted from the phosphor 161 arranged in the vicinity of the subject part, and fluorescence (return light) including the wavelength bands FW1 and FW2 is guided and enters to the image pickup unit 20.

The image pickup unit 20 picks up an image of the fluorescence guided by the rigid insertion portion 30 to generate a fluorescence image, performs the predetermined signal processing on the generated fluorescence image, and outputs the resulting fluorescence image to the image processing apparatus 3.

The fluorescence image input controller 32 temporarily stores the fluorescence image for each frame, which is outputted from the image pickup unit 20. Then, the fluorescence image stored in the fluorescence image input controller 32 is stored in the memory 34 via the bus BS.

The image processing section 33 reads the fluorescence image stored in the memory 34, and performs the predetermined image processing on the read fluorescence image and outputs the resulting read fluorescence image to the bus BS.

Here, at the point of time when the predetermined image processing is performed by the image processing section 33, a fluorescence image allowing a state of generation of the fluorescence in the wavelength band FW1 in the fluorescence region and a state of generation of the fluorescence in the wavelength band FW2 in the phosphor 161 (drawn in the form of a strip shape), for example, such as illustrated in FIG. 7, to be viewed, respectively, and allowing almost no objects other than those to be viewed can be obtained. Note that in FIG. 7, the treatment portion 6a and the shaft portion 6b, which are objects that can substantially not be viewed when the fluorescence image is visualized, are indicated by dotted lines for the sake of convenience.

On the other hand, the CPU 38 reads information on the wavelength band FW1 of fluorescence emitted from the fluorescent medical agent, information on the wavelength band FW2 of fluorescence emitted from the phosphor 161, and shape information including a two-dimensional shape of the phosphor 161 and an actual size of the two-dimensional shape (for example, a value of an actual length WS) from the information storing section 39, and performs processing based on the respective read information pieces and the fluorescence image outputted from the image processing section 33, to obtain observation assist information for assisting the fluorescence observation. In other words, in the present embodiment, the information on the wavelength band FW1 of fluorescence emitted from the fluorescent medical agent, the information on the wavelength band FW2 of fluorescence emitted from the phosphor 161, and the shape information including the two-dimensional shape of the phosphor 161 and the actual size of the two-dimensional shape (for example, the value of an actual length WS) are stored in the information storing section 39 in advance.

Here, specific processing for obtaining observation assist information, which is performed by the CPU 38, will be described taking a case where the fluorescence image illustrated in FIG. 7 is used for the processing, as an example.

First, from among relatively-high luminance (bright) regions in the fluorescence image, the CPU 38 detects a region drawn in a shape matching or substantially matching the shape information as a draw region of the phosphor 161 based on the information on the wavelength band FW1 of fluorescence emitted from the fluorescent medical agent, the information on the wavelength band FW2 of fluorescence emitted from the phosphor 161, and the shape information for the phosphor 161 including the two-dimensional shape of the phosphor 161 and a value of a predetermined actual length of the two-dimensional shape (for example, the value of an actual length WS), and further detects a region drawn in a shape that is largely different from the shape information as a draw region of the fluorescence region.

Next, the CPU 38 calculates a draw width WA of the phosphor 161 drawn in the fluorescence image (see FIG. 7) based on the shape information for the phosphor 161 and the result of detection of the draw region of the phosphor 161 in the fluorescence image, and further performs an operation to divide the calculated draw width WA by the actual length WS (WA/WS) to obtain a value of a scaling factor RA. In other words, the aforementioned scaling factor RA is calculated as a value resulting from standardization of a size of the phosphor 161 in the fluorescence image with reference to the actual size of the phosphor 161 or a value corresponding to a magnification of the drawing of the phosphor 161 in the fluorescence image where the actual size of the phosphor 161 is 1.

On the other hand, the CPU 38 calculates a draw width LX in a horizontal direction of the fluorescence region and a draw width LY in a vertical direction of the fluorescence region, based on the result of detection of the draw region of the fluorescence region in the fluorescence image.

Also, the CPU 38 calculates a value of a horizontal width SX obtained by performing an operation to divide the draw width LX by the scaling factor RA (LX/RA) as an estimated value of an actual length of a horizontal width of the fluorescence region (lesion part) and calculates a value of a vertical width SY obtained by performing an operation to divide multiply the draw width LY by the scaling factor RA (LY/RA) as an estimate value of an actual length of a vertical width of the fluorescence region (lesion part). In other words, the CPU 38 estimates an actual size of the fluorescence region (lesion part) from the values of the horizontal width SX and the vertical width SY (as observation assist information) calculated by performing the above-described operation.

Figure 8:
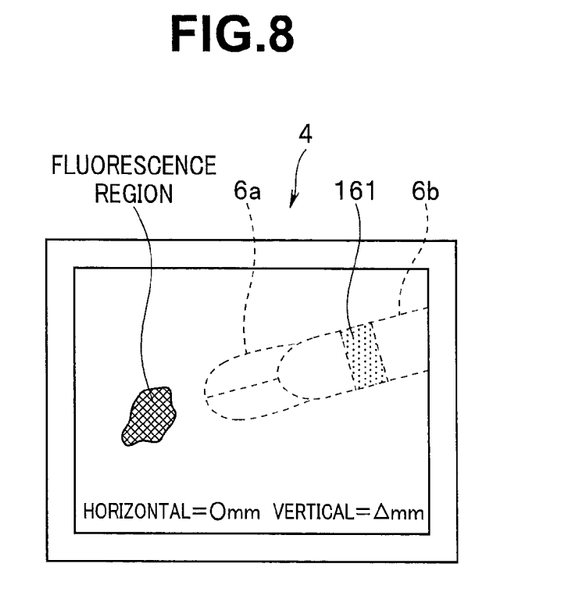
FIG. 8 is a diagram illustrating an example of a display mode of a fluorescence image processed by the image processing apparatus according to the present embodiment.

Subsequently, the CPU 38 controls the display control section 35 to display the horizontal width SX and the vertical width SY obtained as described above together with the fluorescence image outputted from the image processing section 33. FIG. 8 is a diagram illustrating an example of a display mode of a fluorescence image processed by the image processing apparatus according to the present embodiment.

Under the control of the CPU 38, the display control section 35 superimposes information indicating the values of the horizontal width SX and the vertical width SY on the fluorescence image outputted from the image processing section 33, to generate a video signal and outputs the generated video signal to the monitor 4. As a result of such an operation of the display control section 35, an observation image in a display mode, for example, such as illustrated in FIG. 8, is displayed on the monitor 4. Note that in FIG. 8, the treatment portion 6a and the shaft portion 6b, which are objects that can substantially not be viewed on a screen of the monitor 4, are indicated by dotted lines for the sake of convenience.

In the observation image in the display mode illustrated in FIG. 8 as an example, together with the fluorescence image outputted from the image processing section 33, the information indicating the value of the horizontal width SX is displayed as "HORIZONTAL=○ mm" on the monitor 4, and the information indicating the value of the vertical width SY is displayed as "VERTICAL=Δ mm" on the monitor 4. In other words, a surgeon or the like can estimate an actual size of the fluorescence region (lesion part) by viewing the observation image displayed on the monitor 4 as illustrated in FIG. 8, and further can easily determine whether or not a forceps suitable for the actual size of the fluorescence region (lesion part) is used. As a result, time consumed for treatment of the lesion included in the fluorescence image can be reduced in compared with the conventional techniques. Also, the surgeon or the like can easily estimate the actual size of the fluorescence region (lesion part) by viewing the observation image displayed on the monitor 4 as illustrated in FIG. 8. As a result, preferable treatment according to the size of the fluorescence region (lesion part) can be performed.

Note that the CPU 38 is not limited to one that obtains the values of the horizontal width SX and the vertical width SY as observation assist information, and may be one that, for example, where table data TB1 indicating a correlation between an average luminance value of the fluorescence region and an actual distance from the distal end portion of the rigid insertion portion 30 and table data TB2 indicating a correlation between an average luminance value of the phosphor 161 and an actual distance from the distal end portion of the rigid insertion portion 30 are stored in the information storing section 39 in advance, can further obtain a value of a distance SZ corresponding to an estimated value of an actual distance between the fluorescence region and the phosphor 161 as observation assist information.

More specifically, the CPU 38 calculates, based on a result of detection of a draw region of a fluorescence region in the fluorescence image outputted from the image processing section 33, an average luminance value of the draw region obtained as the result of detection, and further obtains, based on a result of comparison between the calculated average luminance value and the aforementioned table data TB1, a distance L1 from the distal end portion of the rigid insertion portion 30, which corresponds to the calculated average luminance value.

Also, the CPU 38 calculates, based on the result of detection of a draw region of the phosphor 161 in the fluorescence image outputted from the image processing section 33, an average luminance value of the draw region obtained as the result of detection, and further obtains, based on a result of comparison between the calculated average luminance value and the aforementioned table data TB2, a distance L2 from the distal end portion of the rigid insertion portion 30, which corresponds to the calculated average luminance value.

Then, the CPU 38 calculates a value of the distance SZ that can be obtained by performing an operation to subtract a value of the distance L2 from a value of the distance L1 (L1−L2) as an estimated value of the actual distance between the fluorescence region and the phosphor 161. In other words, the CPU 38 estimates the actual distance between the fluorescence region and the phosphor 161 based on the value of the distance SZ (as observation assist information) calculated by performing the above-described operation.

Note that the CPU 38 is not limited to one that performs an operation to calculate the value of the distance SZ using the aforementioned table data TB1 and TB2, and may be one that performs the operation to calculate the value of the distance SZ based on, for example, a result of comparison between the average luminance value of the draw region of the fluorescence region and the average luminance value of the draw region of the phosphor 161. According to such operation, for example, as the aforementioned two types of average luminance values become relatively closer to each other, the value obtained as the distance SZ becomes closer to zero, and as a difference between the aforementioned two types of average luminance values becomes relatively greater, the value obtained as the distance SZ increases further from zero.

Figure 9:
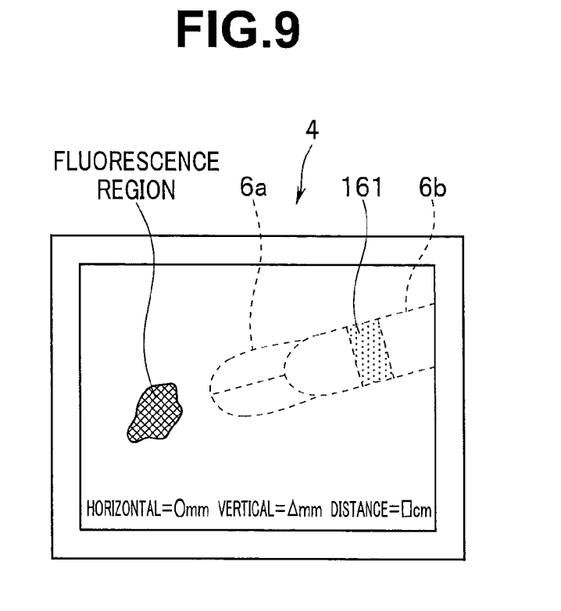
FIG. 9 is a diagram illustrating an example of a display mode of a fluorescence image processed by the image processing apparatus according to the present embodiment, which is different from that in FIG. 8.

On the other hand, the CPU 38 controls the display control section 35 to display the horizontal width SX, the vertical width SY and the distance SZ together with the fluorescence image outputted from the image processing section 33. FIG. 9 is a diagram illustrating an example of a display mode of a fluorescence image processed by the image processing apparatus according to the present embodiment, which is different from that in FIG. 8.

Under the control of the CPU 38, the display control section 35 superimposes the horizontal width SX, the vertical width SY and the distance SZ on the fluorescence image outputted from the image processing section 33 to generate a video signal, and outputs the generated video signal to the monitor 4. As a result of such operation of the display control section 35, an observation image in a display mode, for example, such as illustrated in FIG. 9, is displayed on the monitor 4. Note that in FIG. 9, the treatment portion 6a and the shaft portion 6b, which are objects that can substantially not be viewed on the screen of the monitor 4, are indicated by dotted lines for the sake of convenience.

In the observation image in the display mode illustrated in FIG. 9 as an example, together with the fluorescence image outputted from the image processing section 33, the information indicating the horizontal width SX is displayed as "HORIZONTAL=○ mm" on the monitor 4, the information indicating the vertical width SY is displayed as "VERTICAL=Δ mm" on the monitor 4, and further, information indicating the distance SZ is displayed as "DISTANCE=□ cm" on the monitor 4. In other words, a surgeon or the like can estimate an actual size of the fluorescence region (lesion part) with good accuracy by viewing the observation image displayed on the monitor 4 as illustrated in FIG. 9, and can further easily determine whether or not a forceps suitable for the actual size of the fluorescence region (lesion part) is used. As a result, time consumed for treatment of the lesion included in the fluorescence image can be reduced compared with the conventional techniques. Also, the surgeon or the like can easily estimate the actual size of the fluorescence region (lesion part) by viewing the observation image displayed on the monitor 4 as illustrated in FIG. 9. As a result, preferable treatment according to the size of the fluorescence region (lesion part) can be performed.

Note that the CPU 38 is not limited to one that obtains the horizontal width SX and the vertical width SY as observation assist information, and may be one that further obtains various information that can be used for estimation of the actual size of the fluorescence region as observation assist information, based on, for example, the scaling factor RA calculated as described above and the result of detection of the draw region of the fluorescence region in the fluorescence image.

More specifically, the CPU 38 may be one that further obtains, for example, any one piece of information from among an estimated value of the actual area of the fluorescence region, an estimated value of a width in a major axis direction, an estimated value of a width in a minor axis direction, an estimated position of a center point and an estimated position of a gravity point, which are obtained by respective operations based on the scaling factor RA calculated as described above and the result of detection of the draw region of the fluorescence region in the fluorescence image, as observation assist information that can be used for estimation of the actual size of the fluorescence region.

Figure 10:
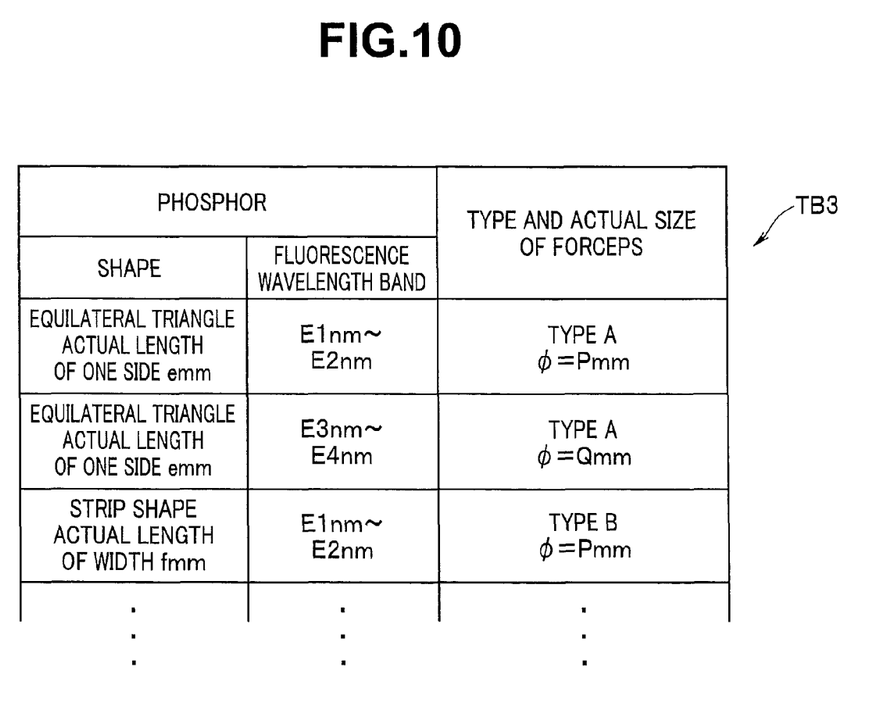
FIG. 10 is a diagram illustrating an example of table data used in processing performed by the image processing apparatus according to the present embodiment.

FIG. 10 is a diagram illustrating an example of table data used in processing performed by the image processing apparatus according to the present embodiment.

Note that, the CPU 38 may be one that where table data TB3 in which a correspondence relation between shape information on the phosphor 161 and information on a wavelength band FW2 of fluorescence emitted from the phosphor 161 is associated with each of a plurality of forceps types, for example, such as illustrated in FIG. 10, is stored in the information storing section 39 in advance, identifies a type and an actual size of the forceps 6 presumed to be included in the fluorescence image, based on the table data TB3 and a result of detection of the draw region of the phosphor 161, and obtains observation assist information according to a result of the identification. FIG. 10 illustrates an example of the table data TB3 where the shape of the phosphor 161 (shape information) and the type of the forceps 6 are correspondingly related to each other and the wavelength band (wavelength band FW2) of fluorescence from the phosphor 161 and the actual diameter of the forceps 6 (actual thickness of the shaft portion 6b) are related to each other.

Furthermore, the CPU 38 may be one that identifies a type and an actual size of the forceps 6 presumed to be included in the fluorescence image based on the aforementioned table data TB3 and the result of detection of the draw region of the phosphor 161, and if the CPU 38 detects that the identified actual size of the forceps 6 is largely different from the horizontal width SX and the vertical width SY, further controls the display control section 35 so as to display, e.g., a character string to provide information to the effect that the treatment efficiency would be enhanced by changing the (currently-used) forceps 6 to another forceps, to a surgeon or the like.

Figure 11:
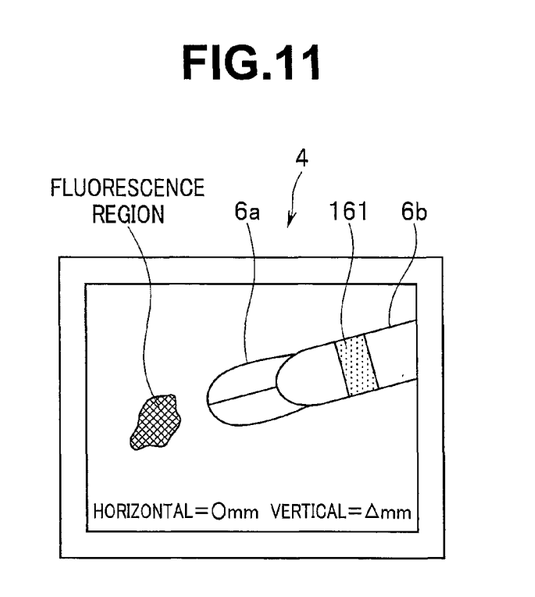
FIG. 11 is a diagram illustrating an example of a display mode of a fluorescence image processed by the image processing apparatus according to the present embodiment, which is different from those in FIGS. 8 and 9.

FIG. 11 is a diagram illustrating an example of a display mode of a fluorescence image processed by the image processing apparatus according to the present embodiment, which is different from those in FIGS. 8 and 9.

On the other hand, the CPU 38 may be one that where, for example, table data TB4 in which a correspondence relation among shape information on the phosphor 161, information on a wavelength band FW2 of fluorescence emitted from the phosphor 161, an outer appearance shape of the forceps provided with the phosphor 161 and a disposed position of the phosphor 161 on the outer appearance shape of the forceps is associated with each of a plurality of forcipes is stored in the information storing section 39 in advance, identifies a type, an actual size and an orientation of the forceps 6 presumed to be included in the fluorescence image, based on the table data TB4 and the result of detection of the draw region of the phosphor 161 and controls the display control section 35 to display a virtual image of an outer appearance shape of the forceps 6 according to a result of the identification. As a result of such control, an observation image in which a position of the treatment portion 6a relative to a position of the fluorescence region can be estimated, for example, such as illustrated in FIG. 11, is displayed on the monitor 4.

Note that the CPU 38 may be one that where, for example, the CPU 38 detects that a plurality of at least one of (draw regions) of fluorescence regions or (draw regions) of phosphors 161 exist in a fluorescence image, performs at least one of processing for providing numbers of, e.g., 1, 2, 3, ... to the respective detected fluorescence regions and (or) the respective detected phosphors 161, respectively, processing for providing symbols (names) of, e.g., A, B, C, ... to the respective detected fluorescence regions and (or) the respective detected phosphors 161 and processing for ranking the respective detected fluorescence regions and (or) the respective detected phosphors 161 in order of capability of meeting a predetermined condition.

Figure 12:
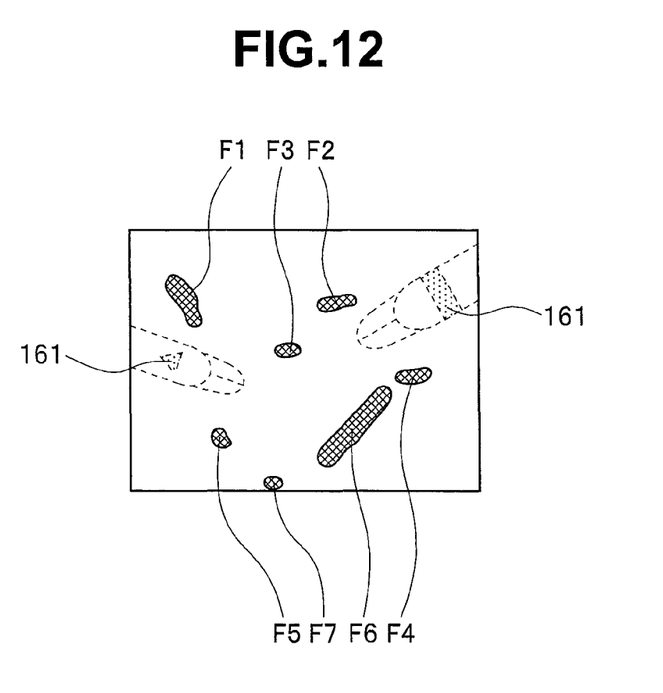
FIG. 12 is a diagram illustrating an example of a fluorescence image used in processing performed by the image processing apparatus according to the present embodiment, which is different from that in FIG. 7.
Figure 13:
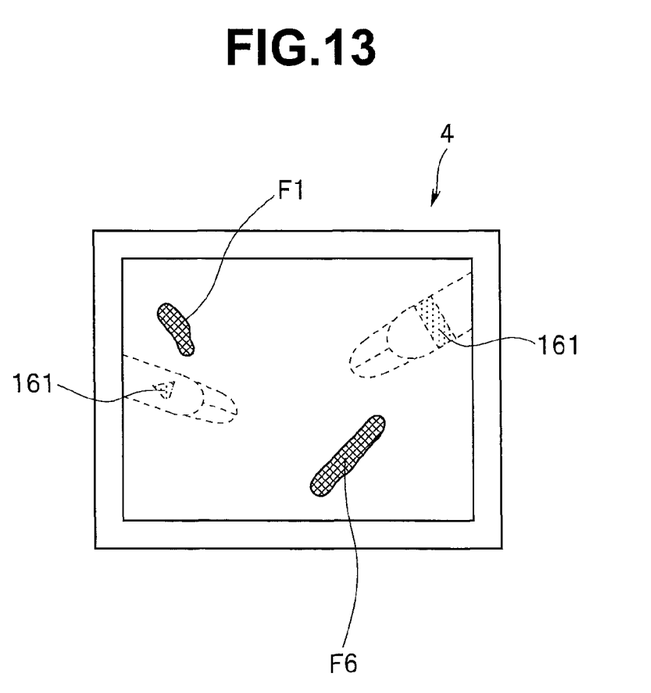
FIG. 13 is a diagram illustrating an example of a display mode of a fluorescence image processed by the image processing apparatus according to the present embodiment, which is different from those in FIGS. 8, 9 and 11.

Also, the CPU 38 may be one that where, for example, the CPU 38 detects that a plurality of at least one of (draw regions) of fluorescence regions or (draw regions) of phosphors 161 exist in a fluorescence image, controls the display control section 35 to display only a fluorescence region and (or) a phosphor 161 meeting a predetermined condition from among the respective detected fluorescence regions and (or) the respective detected phosphors 161. FIG. 12 is a diagram illustrating an example of a fluorescence image used in processing performed by the image processing apparatus according to the present embodiment, which is different from that in FIG. 7. FIG. 13 is a diagram illustrating an example of a display mode of a fluorescence image processed by the image processing apparatus according to the present embodiment, which is different from those in FIGS. 8, 9 and 11.

More specifically, the CPU 38 may calculate respective vertical widths SY of a plurality of fluorescence regions F1 to F7 in a fluorescence image (observation image), for example, such as illustrated in FIG. 12, and control the display control section 35 to display only fluorescence regions whose calculated vertical widths SY are equal to or exceed a predetermined value (only F1 and F6 in FIG. 12) to display a fluorescence image (observation image) such as illustrated in FIG. 13 on the monitor 4. Note that in FIGS. 12 and 13, the treatment portion 6a and the shaft portion 6b, which are objects that can substantially not be viewed on the screen of the monitor 4, are indicated by dotted lines for the sake of convenience.

Note that the aforementioned predetermined condition is not limited to one based on the vertical width SY and may be set based on at least one of respective values (e.g., the horizontal width SX and the luminance value) obtained in the present embodiment (and modifications thereof).

Figure 14:
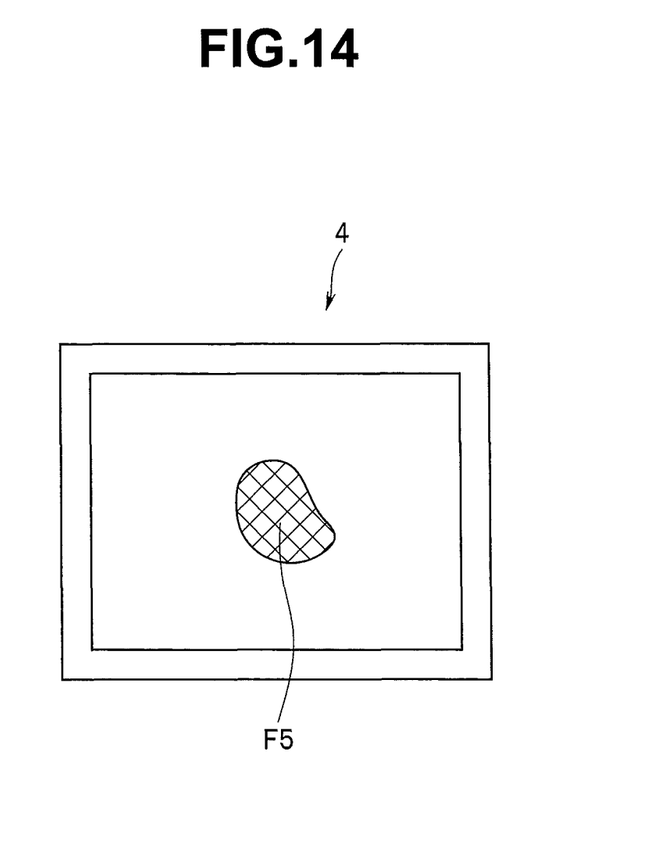
FIG. 14 is a diagram illustrating an example of a display mode of a fluorescence image processed by the image processing apparatus according to the present embodiment, which is different from those in FIGS. 8, 9, 11 and 13.

Also, the CPU 38 may be one that where, for example, the CPU 38 detects that a plurality of at least one of (draw regions) of fluorescence regions or (draw regions) of phosphors 161 exist in a fluorescence image, controls the display control section 35 to display one desired fluorescence region or phosphor 161 selected by an input operation via the input operation section 36 in a predetermined display mode. FIG. 14 is a diagram illustrating an example of a display mode of a fluorescence image processed by the image processing apparatus according to the present embodiment, which is different from those in FIGS. 8, 9, 11 and 13.

More specifically, the CPU 38 may be configured to, if, for example, the CPU 38 detects that a fluorescence region F5 is selected from the plurality of fluorescence regions F1 to F7 in the fluorescence image (observation image) such as illustrated in FIG. 12 based on an instruction outputted from the input operation section 36, control the display control section 35 to provide enlarged display of the selected fluorescence region F5 to display a fluorescence image (observation image) such as illustrated in FIG. 14 on the monitor 4.

Note that the aforementioned predetermined display mode is not limited to one that provides enlarged display of one desired fluorescence region or phosphor 161 selected by an input operation via the input operation section 36, and, for example, may be one that provides display with the one desired fluorescence region or phosphor 161 centered or one that provides display following the one desired fluorescence region or phosphor 161.

The present invention is not limited to the above-described embodiment and modifications, and it should be understood that various alterations and applications are possible without departing from the spirit of the invention.

What is claimed is:

1. An endoscope apparatus comprising:
a light source apparatus that emits excitation light in a wavelength band including a first wavelength band for exciting a first fluorescent substance accumulated in a subject part inside a body cavity and a second wavelength band that is different from the first wavelength band;
an image pickup section configured so as to pick up an image of first fluorescence emitted when the first fluorescent substance accumulated in the subject part is excited by light in the first wavelength band and an image of second fluorescence emitted when a second fluorescent substance provided on a treatment instrument via which treatment of the subject part is performed is excited by light in the second wavelength band, to generate a fluorescence image;
an information storing section that stores shape information including information on a shape and size of the second fluorescent substance; and
an operation section that performs an operation to calculate a scaling factor based on the shape information and a size of a draw region of the second fluorescence in the fluorescence image, and further performs an operation to estimate a size of a region in which the first fluorescence is generated, based on the calculated scaling factor and a size of a draw region of the first fluorescence in the fluorescence image.

2. The endoscope apparatus according to claim 1, wherein the operation section calculates the scaling factor based on a length of the draw region of the second fluorescence in the fluorescence image and on a length of the second fluorescent substance in the shape information, calculates a horizontal width of the region in which the first fluorescence is generated based on a horizontal width of the draw region of the first fluorescence in the fluorescence image and on the scaling factor, calculates a vertical width of the region in which the first fluorescence is generated based on a vertical width of the draw region of the first fluorescence in the fluorescence image and on the scaling factor, and estimates a size of the region in which the first fluorescence is generated as a size based on values of the horizontal width and vertical width of the region in which the first fluorescence is generated.

3. The endoscope apparatus according to claim 1,
wherein the information storing section stores table data in which the shape information and a wavelength band of the second fluorescence are associated with each other for each of a plurality of types of treatment instruments; and
wherein the operation section identifies the type of the treatment instrument presumed to be included in the fluorescence image, based on the table data.

4. The endoscope apparatus according to claim 3, wherein the operation section identifies the type of the treatment instrument presumed to be included in the fluorescence image, based on the table data, and further performs control for displaying a virtual image of an outer appearance shape of the treatment instrument according to a result of the identification.

5. The endoscope apparatus according to claim 1, wherein if the operation section detects that a plurality of the draw regions of the first fluorescence exist in the fluorescence image, the operation section performs control to display only a draw region that meets a predetermined condition from among the respective detected draw regions.

6. The endoscope apparatus according to claim 1, wherein if the operation section detects that a plurality of the draw regions of the first fluorescence exist in the fluorescence image, the operation section performs control to display one desired draw region selected from among the respective detected draw regions, in a predetermined display mode.

7. The endoscope apparatus according to claim 1, wherein if the operation section detects that a plurality of the draw regions of the second fluorescence exist in the fluorescence image, the operation section performs control to display only a draw region that meets a predetermined condition from among the respective detected draw regions.

8. The endoscope apparatus according to claim 1, wherein if the operation section detects that a plurality of the draw regions of the second fluorescence exist in the fluorescence image, the operation section performs control to display one desired draw region selected from among the respective detected draw regions, in a predetermined display mode.

9. The endoscope apparatus according to claim 1, wherein if the operation section detects that a plurality of the draw regions of the first fluorescence exist in the fluorescence image, the operation section performs at least one of processing for ranking the respective detected draw regions in order of capability of meeting a predetermined condition and processing for providing a symbol to each of the detected draw regions.

10. The endoscope apparatus according to claim 1, wherein the operation section estimates the size of the region in which the first fluorescence is generated, by performing an operation to obtain a value relating to at least either one of a width and an area of the region in which the first fluorescence is generated.

11. A medical system comprising:
a light source apparatus that emits excitation light in a wavelength band including a first wavelength band for exciting a first fluorescent substance accumulated in a subject part inside a body cavity and a second wavelength band that is different from the first wavelength band;
a treatment instrument including a second fluorescent substance that is excited by light in the second wavelength band, the treatment instrument being configured so as to enable treatment of the subject part to be performed;
an image pickup section configured so as to pick up an image of first fluorescence emitted, upon application of the excitation light, from the first fluorescent substance accumulated in the subject part, and an image of second fluorescence emitted, upon the application of the excitation light, from the second fluorescent substance arranged in a vicinity of the subject part, to generate a fluorescence image;
an information storing section that stores shape information including information on a shape and size of the second fluorescent substance; and
an operation section that performs an operation to calculate a scaling factor based on the shape information and a size of a draw region of the second fluorescence in the fluorescence image, and further performs an operation to estimate a size of a region in which the first fluorescence is generated, based on the calculated scaling factor and a size of a draw region of the first fluorescence in the fluorescence image.

12. The medical system according to claim 11, wherein the operation section calculates the scaling factor based on a length of the draw region of the second fluorescence in the fluorescence image and on a length of the second fluorescent substance in the shape information, calculates a horizontal width of the region in which the first fluorescence is generated based on a horizontal width of the draw region of the first fluorescence in the fluorescence image and on the scaling factor, calculates a vertical width of the region in which the first fluorescence is generated based on a vertical width of the draw region of the first fluorescence in the fluorescence image and on the scaling factor, and estimates a size of the region in which the first fluorescence is generated as a size based on values of the horizontal width and vertical width of the region in which the first fluorescence is generated.

13. The medical system according to claim 11,
wherein the information storing section stores table data in which the shape information and a wavelength band of the second fluorescence are associated with each other for each of a plurality of types of treatment instruments; and
wherein the operation section identifies the type of the treatment instrument presumed to be included in the fluorescence image, based on the table data.

14. The medical system according to claim 13, wherein the operation section identifies the type of the treatment instrument presumed to be included in the fluorescence image, based on the table data, and further performs control for displaying a virtual image of an outer appearance shape of the treatment instrument according to a result of the identification.

15. The medical system according to claim 11, wherein if the operation section detects that a plurality of the draw regions of the first fluorescence exist in the fluorescence image, the operation section performs control to display only a draw region that meets a predetermined condition from among the respective detected draw regions.

16. The medical system according to claim 11, wherein if the operation section detects that a plurality of the draw regions of the first fluorescence exist in the fluorescence image, the operation section performs control to display one desired draw region selected from among the respective detected draw regions, in a predetermined display mode.

17. The medical system according to claim 11, wherein if the operation section detects that a plurality of the draw regions of the second fluorescence exist in the fluorescence image, the operation section performs control to display only a draw region that meets a predetermined condition from among the respective detected draw regions.

18. The medical system according to claim 11, wherein if the operation section detects that a plurality of the draw regions of the second fluorescence exist in the fluorescence image, the operation section performs control to display one desired draw region selected from among the respective detected draw regions, in a predetermined display mode.

19. The medical system according to claim 11, wherein if the operation section detects that a plurality of the draw regions of the first fluorescence exist in the fluorescence image, the operation section performs at least one of processing for ranking the respective detected draw regions in order of capability of meeting a predetermined condition and processing for providing a symbol to each of the detected draw regions.

20. The medical system according to claim 11, wherein the operation section estimates the size of the region in which the first fluorescence is generated, by performing an operation to obtain a value relating to at least either one of a width and an area of the region in which the first fluorescence is generated.

* * * * *